United States Patent [19]

Schmidt

[11] 4,177,213
[45] Dec. 4, 1979

[54] PROCESS FOR BENZYLATING KETONES

[75] Inventor: Andreas Schmidt, Reinach, Switzerland

[73] Assignee: Ciba-Geigy Corporation, Ardsley, N.Y.

[21] Appl. No.: 833,941

[22] Filed: Sep. 16, 1977

Related U.S. Application Data

[63] Continuation of Ser. No. 682,000, Apr. 30, 1976, abandoned, which is a continuation-in-part of Ser. No. 517,356, Oct. 23, 1974, abandoned.

[30] Foreign Application Priority Data

Nov. 1, 1973 [CH] Switzerland .................. 15404/73

[51] Int. Cl.$^2$ ............................................. C07C 45/00
[52] U.S. Cl. ............................ 260/590 R; 260/590 E; 260/592; 260/590 C; 260/590 D; 260/590 FA; 260/45.95 H; 252/351
[58] Field of Search .............. 260/590 R, 590 E, 592, 260/590 C, 590 D, 590 FA

[56] References Cited

U.S. PATENT DOCUMENTS

| | | | |
|---|---|---|---|
| 3,678,095 | 7/1972 | Dexter | 260/590 R |
| 3,821,334 | 6/1974 | Schmidt et al. | 260/590 R |

Primary Examiner—James H. Reamer
Attorney, Agent, or Firm—Joseph F. DiPrima

[57] ABSTRACT

Benzylated ketones are obtained by reacting corresponding non-benzylated ketones with N,N-dialkyldithiocarbamic acid p-hydroxybenzyl esters in the presence of a base. The compounds are stabilizers for organic material.

5 Claims, No Drawings

PROCESS FOR BENZYLATING KETONES

This is a continuation of application Ser. No. 682,000 filed on Apr. 30, 1976, now abandoned, which is a continuation-in-part of application Ser. No. 517,356 filed on Oct. 23, 1974, now abandoned.

The present invention relates to a process for the manufacture of compounds of the formula I

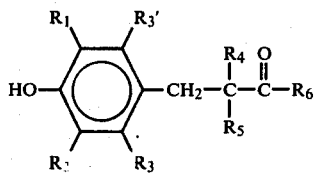

in which $R_1$ denotes a straight-chain or branched alkyl group, a cycloalkyl group or an aralkyl group, $R_2$ denotes hydrogen, a straight-chain or branched alkyl group, a cycloalkyl group or an aralkyl group, $R_3$ and $R_3'$ independently of one another denote hydrogen or a lower alkyl group, or $R_1$ conjointly with $R'_3$, or $R_2$ conjointly with $R_3$, denote tetramethylene, $R_4$ and $R_5$ independently of one another denote hydrogen, phenyl or alkyl or conjointly denote alkylene, and $R_6$ denotes alkyl, phenyl or alkylphenyl or, conjointly with $R_4$ or $R_5$, denotes alkylene or, conjointly with $R_4$ and $R_5$, denotes alkanetriyl, characterised in that 1 mol of a compound of the formula II

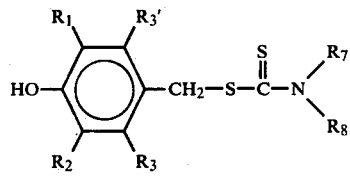

wherein $R_1$, $R_2$, $R_3$ and $R'_3$ have the meaning indicated above and $R_7$ and $R_8$ independently of one another denote a straight-chain or branched alkyl group or, conjointly, with the inclusion of the nitrogen atom, denote a saturated heterocyclic ring, is reacted in the presence of a base with 1 mol of a compound of the formula III

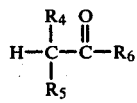

wherein $R_4$, $R_5$ and $R_6$ have the meaning indicated above.

It is known, for example from Belgian Patent Specification No. 781,815, to use compounds of the formula II for benzylating "active methylene compounds", that is to say compounds in which a carbon atom, carrying at least one hydrogen atom, carries at least two activating groups, such as ester groups, keto groups, carboxylic acid amide groups, nitrile groups, sulphonyl groups or phosphonate groups. Such benzylations therefore relate to compounds such as acetoacetic ester, malonic ester, acetylacetone and the like.

It has been found, surprisingly, that the compounds of the formula II are also suitable for benzylating carbonyl compounds of the formula III in which the carbon atom to be substituted is only flanked by a single activating ketone group.

In comparison with other previously known processes for the manufacture of the compounds of the formula I, such as, for example the process described in Belgian Patent Specification No. 626,852, the process according to the invention has a number of general advantages. The starting compounds of the formula II can be prepared easily and are stable and can be reacted even in solvents containing water. The compounds of the formula I can be prepared from the compounds of the formula II in a single process stage. In addition, the starting compounds of the formula II do not need to be isolated, but can be directly reacted with a compound of the formula III, after they have been prepared from a corresponding phenol, a corresponding amine, formaldehyde and carbon disulphide. The compounds of the formula I are therefore accessible in a one-pot process from the corresponding phenols by means of a variant of the process according to the invention. The process according to the invention has a broad spectrum of application, since a large number of ketones can be reacted to give the compounds of the formula I.

Finally, the process according to the invention produces the end products of the formula I in a good yield and, compared with some previously known processes, in a substantially better state of purity.

The alkali metal salt or alkaline earth metal salt of a dithiocarbamic acid, for example

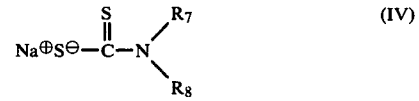

which is split off from the compounds of the formula I during the reaction in the process according to the invention, can, moreover, be used again for preparing the compounds of the formula II.

It is preferentially possible to prepare, by the process according to the invention, compounds of the formula I in which $R_1$ and $R_2$ independently of one another denote a straight-chain or branched alkyl group having 1–4 carbon atoms, or a cycloalkyl group having 6–8 carbon atoms, $R_3$ and $R'_3$ independently of one another denote hydrogen or methyl, $R_4$ and $R_5$ independently of one another denote hydrogen, phenyl or alkyl having 1–8 carbon atoms, or conjointly denote alkylene having 4–11 carbon atoms, and $R_6$ denotes alkyl having 1–17 carbon atoms, phenyl or alkylphenyl having 7–14 carbon atoms, or, conjointly with $R_4$ or $R_5$, denotes alkylene having 3 or 4 carbon atoms, or, conjointly with $R_4$ and $R_5$, denotes alkanetriyl having 5 to 8 carbon atoms.

Compounds of the formula I which are particularly preferentially prepared by the process according to the invention are those in which $R_1$ and $R_2$ independently of one another denote a straight-chain or branched alkyl group having 1–4 carbon atoms, $R_3$ and $R'_3$ denote hydrogen, $R_4$ and $R_5$ independently of one another denote hydrogen or alkyl having 1–8 carbon atoms or conjointly denote alkylene having 4 or 5 carbon atoms, and $R_6$ denotes alkyl having 1–17 carbon atoms, or phenyl or, conjointly with $R_4$ or $R_5$, denotes alkylene having 3 or 4 carbon atoms.

In the process according to the invention, it is preferable to use compounds of the formula II in which $R_1$ and $R_2$ independently of one another denote a straight-chain or branched alkyl group having 1–4 carbon atoms, or a cycloalkyl group having 6–8 carbon atoms, $R_3$ and $R'_3$ independently of one another denote hydrogen or methyl, and $R_7$ and $R_8$ independently of one another denote a straight-chain alkyl group having 1–8 carbon atoms, or conjointly, with the inclusion of the nitrogen atom, denote a saturated, heterocyclic 6-membered ring.

The compounds of the formula I are in part known. The compounds of the formula I in which $R_6$ denotes phenyl or alkylphenyl having 7 to 14 carbon atoms, as well as 2-(3,5-ditert.-butyl-4-hydroxybenzyl)-2-methylcyclohexanone, methyl-[1-(3,5-ditert.butyl-4-hydroxybenzyl)-n-butyl]-ketone and methyl-[1-(3,5-ditert.butyl-4-hydroxybenzyl)-isopropyl]-ketone are new compounds.

Particularly preferred compounds of the formula I, amongst the new compounds, are those in which $R_1$ and $R_2$ independently of one another denote a straight-chain or branched alkyl group having 1–4 carbon atoms, $R_3$ and $R'_3$ denote hydrogen, $R_4$ and $R_5$ independently of one another denote hydrogen or alkyl having 1–8 carbon atoms, or conjointly denote alkylene having 4 or 5 carbon atoms, and $R_6$ denotes phenyl or alkylphenyl having 7 to 14 carbon atoms.

In the definition of the compounds of the formula I, $R_1$, $R_2$, $R_4$, $R_5$, $R_6$, $R_7$ and/or $R_8$ can be alkyl groups.

They can be, for example, methyl, ethyl, ispropyl, n-butyl, sec.-butyl, tert.-butyl, n-amyl, tert.-amyl, sec.-amyl, hexyl, octyl, tert.-octyl, decyl, dodecyl or tetradecyl.

$R_3$ and/or $R'_3$ can be lower alkyl groups, preferably having 1–4 carbon atoms, such as methyl, ethyl, isopropyl, n-butyl, sec.-butyl or tert.-butyl, $R_1$ and/or $R_2$ can also denote cycloalkyl groups, such as cyclopentyl, cyclohexyl, α-methylcyclohexyl or cyclooctyl, $R_1$ and/or $R_2$ can also be aralkyl groups, such as benzyl, α-phenylethyl or α,α-dimethylbenzyl, $R_4$ and $R_5$, $R_4$ and $R_6$ or $R_5$ and $R_6$ respectively can conjointly denote alkylene, such as trimethylene, tetramethylene, pentamethylene, 1-methyltetramethylene or 1,2,2-trimethyl-1,3-cyclopentylene, $R_6$ can be a phenyl substituted in the o-, m- or p-position by alkyl, such as methyl, ethyl, isopropyl, n-butyl, sec.-butyl, tert.-butyl, n-amyl, tert.-amyl, sec.-amyl or hexyl, $R_6$, conjointly with $R_4$ and $R_5$, can be an alkanetriyl, such as 1,5,8-octanetriyl, 1,4,7-heptanetriyl or 1,3,7-heptanetriyl, and $R_7$ and $R_8$, conjointly with the nitrogen atom, can form a saturated heterocyclic structure. Piperidyl and morpholinyl are examples of this.

Examples of compounds of the formula III are: acetone, methyl ethyl ketone, methyl hexyl ketone, methyl heptadecyl ketone, acetophenone, methyl benzyl ketone, 1,1-diphenylacetone, methyl cyclohexyl ketone, cyclohexanone, 2-methylcyclohexanone, 2,6-dimethylcyclohexanone, 1-decalone, diisopropyl ketone and methyl isopropyl ketone.

The process according to the invention can be carried out by initially taking the compounds of the formula II and III in a suitable solvent and adding a solution of the base dropwise at a temperature of, for example, −20° to +150° C., or by initially taking a mixture of the base and the compound of the formula III and adding a solution of the compound of the formula II dropwise. The reaction is preferably carried out at temperatures between 0° and 100° C.

In this the molar ratio of the compounds of the formula II and the base is 1:1 to 1:3, preferably 1:1 to 1:1.5.

The compound of the formula III is used in a molar ratio, relative to the compound of the formula II, of up to a 100-fold excess, preferably in a 1.5- to 3-fold excess.

The concentrations are not critical for the process according to the invention. As far as the individual components are concerned, the concentrations are only limited by the solubility and can be, for example, 0.1–5 mols per liter of solution.

The solvent used in the process according to the invention are, for example, lower alcohols, such as methanol, ethanol or isopropanol or mixtures thereof with water, aromatic hydrocarbons, such as benzene or toluene, ethers, such as diethyl ether, dioxane or tetrahydrofurane, or aliphatic hydrocarbons, such as ligroin. In a preferred embodiment of the process according to the invention the solvents used are lower alcohols or mixtures of said lower alcohols with water. In a more preferred embodiment of the invention, the solvents are lower alcohols selected from methanol, ethanol and isopropanol, especially isopropanol, or mixtures of isopropanol with water.

If, in the process according to the invention, the base is added dropwise, it can be dissolved in one of the abovementioned solvents or in water. Examples of bases which can be used in accordance with the invention are alkali metal amides, such as sodium amide or lithium amide, alkali metal hydrides, such as lithium hydride or sodium hydride, alkali metal hydroxides, such as sodium hydroxide, potassium hydroxide or lithium hydroxide, or alcoholates, such as sodium methylate, sodium ethylate or magnesium diethylate. Examples or particularly advantageous bases useful in the invention are alkali metal hydroxides and alcoholates, particularly alkali metal hydroxides.

The alkali metal salts of the compounds of the formula III can also be employed as bases. They are prepared, for example, by adding an alkali metal such as sodium to a solution of a compound of the formula III in an inert solvent.

In a preferred embodiment of the process according to the invention, the ketone of the formula III is used direct as the solvent. The reaction is carried out by initially taking the base in the compound of the formula III and adding dropwise a solution of a compound of the formula II in the compound of the formula III as the solvent. The reaction is carried out at a temperature of −20° to +150° C., preferably −10° to +40° C.

The abovementioned compounds can be used as the bases; in the simplest case an alkali metal salt of the compound of the formula III itself, which is prepared by dissolving an alkali metal in the compound of the formula III, is used.

In this the molar ratio of the compound of the formula II and the base is 1:1 to 1:2. The base is preferably used in excess.

The starting compounds of the formula II can be prepared, as described in U.S. Pat. No. 1,757,174, from the corresponding 2,6-dialkylphenols, formaldehyde, carbon disulphide and a dialkylamine of the formula $HNR_7R_8$.

The compounds of the formula I are used as stabilisers for organic substrates. They are also valuable intermediate products for the preparation of stabilisers for organic substrates.

For example, stabilisers of the formula V

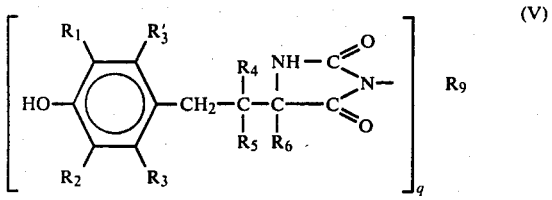

(V)

in which q is 1–3, $R_1$, $R_2$, $R_3$, $R'_3$, $R_4$, $R_5$ and $R_6$ have the same meaning as indicated in the formula I, and, if q=1, $R_9$ represents hydrogen or a substituted or unsubstituted alkyl, alkenyl or cycloalkyl group, if q=2, $R_9$ represents an alkanetriyl group which is optionally interrupted by ester functions, hetero-atoms and/or benzene rings, and, if q=3, $R_9$ represents an alkanetriyl group or a trifunctional group containing a heterocyclic radical, can be obtained by reacting the compounds of the formula I with alkali metal cyanide and ammonium carbonate.

Examples of organic substrates which can be stabilised by the compounds prepared in accordance with the invention or by their secondary products, are:

1. Polymers which are derived from hydrocarbons with single or double unsaturation, such as polyolefines, for example polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylenebutene-1 copolymers, propylene-isobutylene copolymers, styrenebutadiene copolymers and terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, and polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as a comonomer.

7. Polyphenylene oxides.
8. Polyurethanes and polyureas.
9. Polycarbonates.
10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cullulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The compounds of the formula I are incorporated into the substrates in a concentration of 0.005 to 5% by weight calculated relative to the material to be stabilised.

Preferably, 0.01 to 1.0, and particularly preferentially 0.02 to 0.5,% by weight of the compounds, calculated relative to the material to be stabilised, are incorporated into the latter. The incorporation can take place for example by mixing in at least one of the compounds of the formula I and optionally further additives according to the methods customary in the art, before or during shaping, or by applying the dissolved or dispersed compounds to the polymer, if appropriate with subsequent evaporation of the solvent.

In the case of crosslinked polyethylene, the compounds are added before crosslinking.

The compounds of the formula I can also be added before or during the polymerisation.

As further examples of additives together with which the stabilisers of the formula I can be employed, there should be mentioned:

1. Antioxidants 1.1 Simple 2,6-dialkylphenols, such as, for example, 2,6-di-tert.butyl-4-methylphenol, 2-tert.butyl-4,6-dimethylphenol, 2,6-di-tert.butyl-4-methoxymethylphenol and 2,6-dioctadecyl-4-methylphenol.

1.2 Derivatives of alkylated hydroquinones, such as, for example, 2,5-di-tert.butyl-hydroquinone, 2,5-di-tert.amyl-hydroquinone, 2,6-di-tert.butyl-hydroquinone, 2,5-di-tert.butyl-4-hydroxy-anisole, 3,5-di-tert.butyl-4-hydroxy-anisole, tris-(3,5-di-tert.butyl-4-hydroxyphenyl) phosphite, 3,5-di-tert.-butyl-4-hydroxyphenyl) adipate.

1.3 Hydroxylated thiodiphenyl ethers such as, for example, 2,2'-thio-bis-(6-tert.butyl-4-methylphenol), 2,2'-thio-bis-(4-octylphenol), 4,4'-thio-bis-(6-tert.butyl-3-methylphenol), 4,4'-thio-bis-(3,6-di-sec.amylphenol), 4,4'-thio-bis-(6-tert.butyl-2-methylphenol) and 4,4'-bis-(2,6-dimethyl-4-hydroxyphenyl) disulphide.

1.4 Alkyldiene-bisphenols, such as, for example, 2,2'-methylene-bis-(6-tert.butyl-4-methylphenol), 2,2'-methylene-bis-(6-tert.butyl-4-ethylphenol), 4,4'-methylene-bis-(6-tert.butyl-2-methylphenol), 4,4'-methylene-bis-(2,6-ditert.butylphenol), 2,6-di-(3-tert.tuyl-5-methyl-2-hydroxybenzyl)-4-methylphenol, 2,2'-methylene-bis[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butene, 2,2-bis-(5-tert.butyl-4-hydroxy-2-methylphenyl)-butene, 2,2-bis-(3,5-di-tert.butyl-4-hydroxyphenyl)-propane, 1,1,3-tris-(5-tert.butyl-4-hydroxy-2-methylphenyl)-butene, 2,2-bis-(5-tert.butyl-4-hydroxy-2-methylphenyl)-4-n-dodecylmercapto-butane, 1,15,5-tetra-(5-tert.butyl-4-hydroxy-2-methylphenyl)-pentane and ethylene glycol bis-[3,3-bis-(3'-tert.butyl-4'-hydroxyphenyl)-butyrate].

1.5 O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)dithiol terephthalate.

1.6 Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)malonic acid dioctadecyl esters, 2,2-bis-(3,5-di-tert.butyl-4-hydroxybenzyl)-malonic acid didodecylmercaptoethyl-ester and 2,2-bis-(3,5-di-tert.butyl-4-hydroxybenzyl) malonic acid di-[4-(1,1,3,3-tetramethylbutyl)-phenyl]ester.

1.7 Hydroxybenzyl-aromatics, such as, for example, 1,3,5-tri-(3,5-di-tert.butyl-4-hydroxybenzyl)2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxy-anilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10 Esters of β-(3,5-di-tert.butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.11 Esters of β-(5-tert.butyl-4-hydroxy-3-methylphenyl)-propionic acid with monohydric or polyhydric alcohols such as, for example, with methanol, ethanol, octadecanol, 1,6-hexanediol. 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethyl hexanediol, trimethylolethane, trimethylolpropane, trishydroxyethylisocyanurate and 4-hydroxymethyl-1-phospha-2,6,7-trioxabicyclo[2,2,2]octane.

1.12 Esters of 3,5-di-tert.butyl-4-hydroxyphenylacetic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, tris-hydroxyethylisocyanurate and 4-hydroxymethyl-1-phospha-2,6,7-trioxabicyclo[2,2,2]octane.

1.13 Acylaminophenols, such as, for example, N-(3,5-di-tert.butyl-4-hydroxyphenyl)stearic acid amide and N,N'-di-(3,5-ditert.butyl-4-hydroxyphenyl)-thio-bis-acetamide.

1.14 Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15 Aminoaryl derivatives, such as, for example, phenyl-1-naphthylamine, phenyl-2-naphthylamine, N,N'-diphenyl-p-phenylenediamine, N,N'-di-1-naphtyl-p-phenylenediamine, N,N'-di-2-naphthyl-p-phenylenediamine, N,N'-di-sec.butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and diotyliminodibenzyl and polymerised 2,2,4-tri-methyl-1,2-dihydroquinoline.

2. UV absorbers and light stabilisers 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl- or 6-undecylderivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-Bis-(2'-hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester or octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)- phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl ester such as the methyl, ethyl, or butyl ester, nickel complexes of ketoximes, such as of 2-hydroxy-4-methyl-phenyl-undecylketoxime, and nickel 3,5-di-tert-.butyl-4-hydroxybenzoate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate and 3-n-octyl-7,7,9,9-tetramethyl-1,3,8-triazaspiro[4,5]decane-2,4-dione.

2.9. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyloxanilide, 2-ethoxy-2'-ethyl-oxanilide, N,N'-bis-(3-dimethylaminopropyl)oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o-and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.butyl-4-hydroxyphenyl-propionyl)-hydrazine, N-salicylal-N'-salicyloyl-hydrazine and 3-salicyloylamino-1,2,4-triazole.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetraoxa-3,9-diphosphaspiro[5,5]undecane and tri-(4-hydroxy-3,5-di-tert.butylphenyl) phosphite.

5. Compounds which destroy peroxide, such as, for example, esters of β-thiodipropionic acid, for example the lauryl, stearyl, myristyl or tridecyl esters, salts of 2-mercaptobenzimidazole, for example the Zn salt, and diphenylthiourea.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate or K palmitate.

8. PVC stabilisers, such as, for example, organic tin compounds, organic lead compounds and barium-cadmium salts of fatty acids.

9. Nucleating agents, such as, for example, 4-tert.butyl-benzoic acid, adipic acid and diphenylacetic acid.

10. Other additives, such as, for example, plasticisers, lubricants, emulsifiers, fillers, carbon black, asbestos, kaolin, talc, glass fibres, pigments, optical brighteners, flameproofing agents and antistatic agents.

The invention is described in more detail in the examples which follow. Parts therein denote parts by weight and percentages (%) are percentages by weight.

EXAMPLE 1

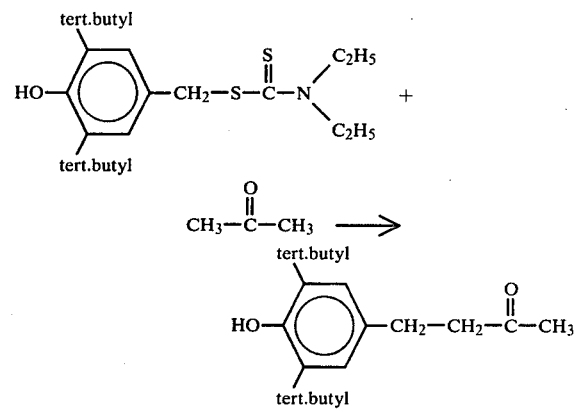

27 g (0.5 mol) of sodium methylate are initially placed in 200 ml of acetone at 0° C. 91.8 g (0.25 mol) of N,N-diethyl-dithiocarbamic acid 3,5-di-tert.butyl-4-hydroxybenzyl ester, dissolved in 200 ml of acetone, are added dropwise over the course of one hour, with good stirring, at the same temperature. The mixture is then stirred for a further 2 hours at room temperature and is then heated under reflux for a further hour. After cooling, 5 ml of glacial acetic acid are added and the mixture is diluted with toluene. The toluene phase is washed twice with water, concentrated completely under reduced pressure and distilled in a high vacuum.

Methyl 3,5-ditert.butyl-4-hydroxy-phenylethyl ketone, which boils at 125°–130° C. at 0.1 mm Hg and solidifies on cooling, is thus obtained in a yield of 87%. Melting point 48° C.

EXAMPLE 2

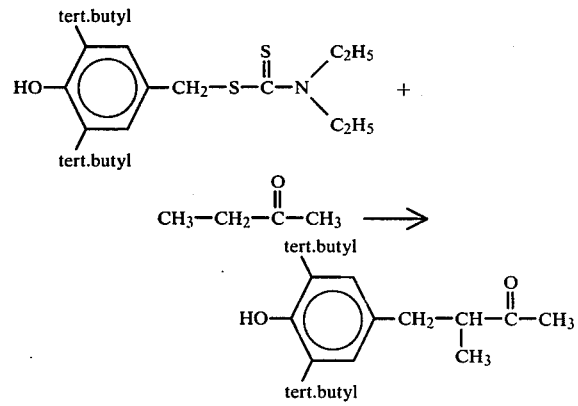

19.14 g (0.852 mol) of sodium cut up into small pieces, are suspended in 1,000 ml of methyl ethyl ketone. After the sodium has gone into solution, 306 g (0.832 mol) of N,N-diethyldithiocarbamic acid 3,5-ditert.butyl-4-hydroxybenzyl ester, dissolved in 700 ml of methyl ethyl ketone, are added dropwise over the course of 2 hours with stirring, at 0° C. The mixture is then heated for one hour under reflux, and 1,000 ml of 1% strength acetic acid are then added and the mixture is extracted with toluene. The organic phase is concentrated completely under reduced pressure and distilled in a high vacuum.

Methyl 2-(3,5-ditert.butyl-4-hydroxyphenyl)-isopropyl ketone, which boils at 125°–135° C. at 0.35 mm Hg and solidifies on cooling, is thus obtained in a yield of 75%. Melting point 75° C.

If, in this example, the methyl ethyl ketone is replaced by an equivalent quantity of cyclohexanone, an otherwise identical procedure gives 2-(3,5-ditert.butyl-4-hydroxybenzyl)-cyclohexanone, melting point 79° C., in a yield of 80%.

EXAMPLE 3

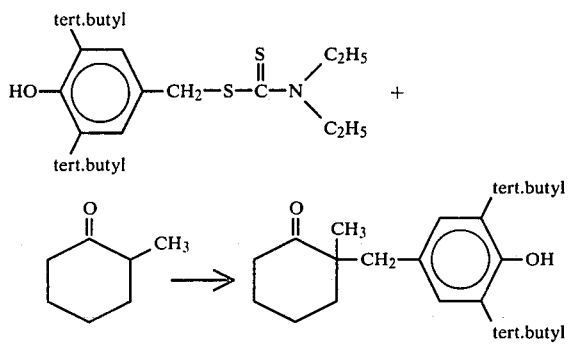

36.7 g (0.1 mol) of N,N-diethyl-dithiocarbamic acid 3,5-ditert.butyl-4-hydroxybenzyl ester and 14.6 g (0.13 mol) of 2-methylcyclohexanone in 150 ml of isopropanol are warmed to 50° C., whilst stirring. A solution of 4 g (0.1 mol) of sodium hydroxide in 10 ml of water is added dropwise over the course of an hour at this temperature. The mixture is then stirred for a further 2 hours at this temperature and cooled and 60 ml of 2% strength acetic acid are added. The mixture is stirred for a further 2 hours at room temperature and then cooled to 10° C. The precipitate which is formed is filtered off and recrystallised from 70% strength isopropanol.

2-(3,5-Ditert.butyl-4-hydroxybenzyl)-2-methyl-cyclohexanone, melting point 75° C., is obtained in this way in a yield of 60%.

If, in this example, the 2-methylcyclohexanone is replaced by an equivalent quantity of isopropyl methyl ketone, an otherwise identical procedure gives methyl [1-(3,5-ditert.-butyl-4-hydroxybenzyl)-isopropyl] ketone, melting point 75° C., in a yield of 65%.

If, in this example, the 2-methylcyclohexanone is replaced by an equivalent quantity of methyl n-butyl ketone, an otherwise identical procedure gives methyl [1-(3,5-ditert.-butyl-4-hydroxybenzyl)-n-butyl] ketone, which boils at 120° C. at 0.01 mm Hg and is an oil, in a yield of 60%.

| Elementary analysis for $C_{21}H_{34}O_2$: | | |
|---|---|---|
| | Calculated(%) | Found(%) |
| C | 79.19 | 78.9 |
| H | 10.76 | 10.9 |
| 0 | 10.05 | 10.1 |

If, in this example, the 2-methylcyclohexanone is replaced by an equivalent quantity of acetophenone, an otherwise identical procedure gives phenyl (3,5-ditert.butyl-4-hydroxyphenylethyl) ketone in a yield of 53%.

EXAMPLE 4

Stabilisation of polypropylene against degradation during processing 0.1 part of methyl [1-(3,5-ditert.butyl-4-hydroxybenzyl)-isopropyl] ketone are homogeneously mixed with 100 parts of polypropylene powder ("Propathene HF 20" of Messrs. ICI) and the product is regranulated 5 times successively in a single screw extruder at a maximum temperature of 260° C. and 100 r.p.m. The melt index (MI) of the material is measured after each of the 1st, 3rd and 5th extrusions (throughput 2,160 g at 230° C.; figures in grams per 10 minutes). Degradation of the polymer manifests itself by a rapid increase of the melt index. An experiment is carried out in the same way, in parallel, in which no stabiliser is added.

| | Melt index | | | |
|---|---|---|---|---|
| | As received | 1st extrusion | 3rd extrusion | 5th extrusion |
| Unstabilised sample | 2.50 | 13.5 | 36.1 | 72.0 |
| Stabilised sample | 2.50 | 4.1 | 6.4 | 7.8 |

What we claim is:

1. A process for the manufacture of compounds of the formula I

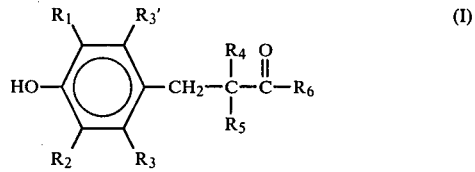

in which $R_1$ denotes a straight-chain or branched alkyl group, a cycloalkyl group or an aralkyl group, $R_2$ denotes hydrogen, a straight-chain or branched alkyl group, a cycloalkyl group or an aralkyl group, $R_3$ and $R'_3$ independently of one another denote hydrogen or a lower alkyl group, or $R_1$ conjointly with $R'_3$, or $R_2$ conjointly with $R_3$, denote tetramethylene, $R_4$ and $R_5$ independently of one another denote hydrogen, phenyl or alkyl or conjointly denote alkylene, $R_6$ denotes alkyl, phenyl or alkylphenyl, or, conjointly with $R_4$ and $R_5$, denotes alkanetriyl, characterised in that 1 mol of a compound of the formula II

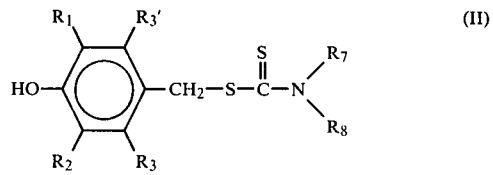

wherein $R_1$, $R_2$, $R_3$ and $R'_3$ have the meaning indicated above and $R_7$ and $R_8$ independently of one another denote a straight-chain or branched alkyl group, or conjointly, with the inclusion of the nitrogen atom, denote a saturated, heterocyclic ring, is reacted in the presence of a base selected from an alkali metal hydroxide or alcoholate at a temperature of −20° C. to +150° C. with one mol of a compound of the formula III

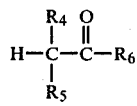
(III)

wherein $R_4$, $R_5$ and $R_6$ have the meaning indicated above.

2. Process according to claim 1, characterised in that, in the formula I, $R_1$ and $R_2$ independently of one another denote a straight-chain or branched alkyl group having 1–4 carbon atoms, or a cycloalkyl group having 6–8 carbon atoms, $R_3$ and $R'_3$ independently of one another denote hydrogen or methyl, $R_4$ and $R_5$ independently of one another denote hydrogen, phenyl or alkyl having 1–8 carbon atoms, or conjointly denote alkylene having 4–11 carbon atoms, and $R_6$ denotes alkyl having 1–17 carbon atoms, phenyl or alkylphenyl having 7–14 carbon atoms, or conjointly with $R_4$ and $R_5$, denotes alkylene having 3 or 4 carbon atoms, or, conjointly with $R_4$ and $R_5$, denotes alkanetriyl having 5 to 8 carbon atoms.

3. Process according to claim 1, characterised in that, in the formula I, $R_1$ and $R_2$ independently of one another denote a straight-chain or branched alkyl group having 1–4 carbon atoms, $R_3$ and $R'_3$ denote hydrogen, $R_4$ and $R_5$ independently of one another denote hydrogen or alkyl having 1–8 carbon atoms or conjointly denote alkylene having 4 or 5 carbon atoms, and $R_6$ denotes alkyl having 1–17 carbon atoms, or phenyl or, conjointly with $R_4$ or $R_5$, denotes alkylene having 3 or 4 carbon atoms.

4. Process according to claim 1, characterised in that, in the formula II, $R_1$ and $R_2$ independently of one another denote a straight-chain or branched alkyl group having 1–4 carbon atoms, or a cycloalkyl group having 6–8 carbon atoms, $R_3$ and $R'_3$ independently of one another denote hydrogen or methyl, and $R_7$ and $R_8$ independently of one another denote a straight-chain alkyl group having 1–8 carbon atoms, or conjointly, with the inclusion of the nitrogen atom, denote a saturated, heterocyclic 6-membered ring.

5. Process according to claim 1, characterised in that the base is alkali metal hydroxide.

* * * * *